US012661321B2

(12) United States Patent
Curtis

(10) Patent No.: US 12,661,321 B2
(45) Date of Patent: *Jun. 23, 2026

(54) SINGLE-INJECTION METHODS AND FORMULATIONS TO INDUCE AND CONTROL MULTIPLE OVARIAN FOLLICLES IN BOVINE, CAPRINE, OVINE, CAMELID AND OTHER FEMALE ANIMALS

(71) Applicant: Therio, LLC, Manhattan, KS (US)

(72) Inventor: John L. Curtis, Manhattan, KS (US)

(73) Assignee: Therio, LLC, Manhattan, KS (US)

( * ) Notice: Subject to any disclaimer, the term of this patent is extended or adjusted under 35 U.S.C. 154(b) by 43 days.

This patent is subject to a terminal disclaimer.

(21) Appl. No.: 18/613,333

(22) Filed: Mar. 22, 2024

(65) Prior Publication Data

US 2024/0226009 A1 Jul. 11, 2024

Related U.S. Application Data

(60) Continuation-in-part of application No. 17/828,412, filed on May 31, 2022, now Pat. No. 11,964,053, which is a division of application No. 15/912,101, filed on Mar. 5, 2018, now Pat. No. 11,376,220.

(60) Provisional application No. 62/527,084, filed on Jun. 30, 2017.

(51) Int. Cl.
| | |
|---|---|
| *A61K 9/10* | (2006.01) |
| *A61K 9/00* | (2006.01) |
| *A61K 9/16* | (2006.01) |
| *A61K 9/50* | (2006.01) |
| *A61K 38/24* | (2006.01) |
| *A61P 5/00* | (2006.01) |

(52) U.S. Cl.
CPC .......... *A61K 9/1647* (2013.01); *A61K 9/0019* (2013.01); *A61K 9/10* (2013.01); *A61K 9/5031* (2013.01); *A61K 38/24* (2013.01); *A61P 5/00* (2018.01)

(58) Field of Classification Search
None
See application file for complete search history.

(56) References Cited

U.S. PATENT DOCUMENTS

| | | | |
|---|---|---|---|
| 3,499,445 A | 3/1970 | Reed | |
| 3,835,108 A | 9/1974 | Goetz et al. | |
| 3,860,701 A | 1/1975 | Short | |
| 4,005,063 A | 1/1977 | Gendrich et al. | |
| 4,008,209 A | 2/1977 | Fujino et al. | |
| 4,159,980 A | 7/1979 | Immer et al. | |
| 4,599,227 A | 7/1986 | Dees et al. | |
| 4,670,419 A | 6/1987 | Uda et al. | |
| 4,762,717 A | 8/1988 | Crowley, Jr. | |
| 4,780,451 A * | 10/1988 | Donaldson | C07K 14/59 |
| | | | 514/9.9 |

| | | | |
|---|---|---|---|
| 4,975,280 A | 12/1990 | Schacht et al. | |
| 5,162,306 A | 11/1992 | Donaldson | |
| 5,429,822 A | 7/1995 | Gresser et al. | |
| 5,512,303 A | 4/1996 | Garza Flores et al. | |
| 5,589,457 A | 12/1996 | Wiltbank et al. | |
| 5,633,014 A | 5/1997 | Garza Flores et al. | |
| 5,650,173 A | 7/1997 | Ramstack et al. | |
| 5,747,058 A | 5/1998 | Tipton et al. | |
| 5,814,342 A | 9/1998 | Okada et al. | |
| 5,941,844 A | 8/1999 | Eckenhoff | |
| 6,028,057 A | 2/2000 | Burns | |
| 6,573,254 B1 | 6/2003 | Kuenzel et al. | |
| 7,151,083 B2 | 12/2006 | Franks et al. | |
| 7,205,281 B2 | 4/2007 | Lauderdale | |
| 7,446,090 B2 | 11/2008 | Hoffmann et al. | |
| 7,563,763 B2 | 7/2009 | Hoffmann et al. | |
| 7,629,113 B2 | 12/2009 | Seidel et al. | |
| 7,740,884 B2 | 6/2010 | Samaritani et al. | |
| 7,741,268 B2 | 6/2010 | Samaritani et al. | |
| 8,518,881 B2 | 8/2013 | Colgin et al. | |
| 8,530,419 B2 | 9/2013 | Lauderdale | |
| 8,905,913 B2 | 12/2014 | Webel et al. | |
| 8,927,496 B2 | 1/2015 | Lauderdale | |
| 8,937,044 B2 | 1/2015 | Lauderdale | |
| 9,018,165 B2 | 4/2015 | Lauderdale | |
| 9,351,818 B2 | 5/2016 | Lauderdale | |
| 9,352,011 B2 | 5/2016 | Webel et al. | |
| 2004/0028733 A1 | 2/2004 | Tracy et al. | |
| 2005/0130894 A1 | 6/2005 | Lauderdale | |

(Continued)

FOREIGN PATENT DOCUMENTS

| | | |
|---|---|---|
| CN | 101129333 A | 2/2008 |
| CN | 104800834 A | 7/2015 |

(Continued)

OTHER PUBLICATIONS

PCT International Search Report for International Application No. PCT/US2018/022067, mailed May 23, 2018, 3pp.
PCT Written Opinion for International Application No. PCT/US2018/022067, mailed May 23, 2018, 5pp.
PCT International Preliminary Report on Patentability for International Application No. PCT/US2018/022067, issued Dec. 31, 2019, 6pp.
European Patent Office, Supplementary European Search Report for European Patent Application No. EP 18825459.3, mailed Mar. 16, 2021, 9pp.
Anik et al. (1984). Delivery Systems for LHRH and analogs, In: Vickery, B.H., Nestor, J.J., Hafez, E.S.E. (eds) LHRH and Its Analogs. Advances in Reproductive Health Care, vol. 1. Springer, Dordrecht. https://doi.org/10.1007/978-94-009-5588-2_33.

(Continued)

*Primary Examiner* — Craig D Ricci
(74) *Attorney, Agent, or Firm* — The Roy Gross Law Firm, LLC; Roy D. Gross

(57) ABSTRACT

Methods and formulations for a simplified, single-injection method to induce and control the synchronous growth (superstimulation), and ovulation (superovulation) of multiple ovarian follicles in bovine, ovine, caprine, camelid and other female animals enabling the subsequent collection of (a) multiple oocytes when conducting in-vitro fertilization, or (b) multiple embryos when conducting multiple ovulation embryo transfer.

9 Claims, No Drawings

(56) References Cited

U.S. PATENT DOCUMENTS

| | | | |
|---|---|---|---|
| 2006/0264372 | A1 | 11/2006 | Webel et al. |
| 2007/0173450 | A1 | 7/2007 | Lauderdale |
| 2007/0197435 | A1 | 8/2007 | Webel |
| 2008/0312151 | A1 | 12/2008 | Colgin et al. |
| 2009/0036384 | A1 | 2/2009 | Bell et al. |
| 2012/0046519 | A1 | 2/2012 | Webel et al. |
| 2013/0041210 | A1 | 2/2013 | Lauderdale |
| 2013/0085321 | A1 | 4/2013 | Lauderdale |
| 2014/0335193 | A1 | 11/2014 | Rintoul et al. |
| 2015/0297726 | A1 | 10/2015 | Yoon et al. |
| 2015/0335713 | A1 | 11/2015 | Souza et al. |
| 2016/0250333 | A1 | 9/2016 | Kimura et al. |
| 2017/0143786 | A1 | 5/2017 | Feenstra et al. |

FOREIGN PATENT DOCUMENTS

| | | | |
|---|---|---|---|
| EP | 0021234 | A1 | 1/1981 |
| EP | 0298990 | A1 | 1/1989 |
| JP | 2005281245 | A | 10/2005 |
| WO | 9516459 | A1 | 6/1995 |

OTHER PUBLICATIONS

Roy et al. Formulation and design of sustained release matrix tablets of metformin hydrochloride: Influence of hypromellose and polyacrylate polymers. Int J Appl Basic Med Res. Jan. 2013;3(1):55-63. doi: 10.4103/2229-516X.112242. PMID: 23776841; PMCID: PMC3678683.

Blasi, P. Poly(lactic acid)/poly(lactic-co-glycolic acid)-based microparticles: an overview. J. Pharm. Investig. 49, 337-346 (2019). https://doi.org/10.1007/s40005-019-00453-z.

Schoubben et al. Meeting the unmet: from traditional to cutting-edge techniques for poly lactide and poly lactide-co-glycolide microparticle manufacturing. J. Pharm. Investig. 49, 381-404 (2019). https://doi.org/10.1007/s40005-019-00446-y.

Packhaeuser et al. In situ forming parenteral drug delivery systems: an overview. Eur J Pharm Biopharm. Sep. 2004;58(2):445-55. doi: 10.1016/j.ejpb.2004.03.003. PMID: 15296966.

Alcivar AA. et al. (1992). Endocrine changes in beef heifers superovulated with follicle stimulating hormone (FSH-P) or human menopausal gonadotropin. J Anim Sci; 70:224-231. https://doi.org/10.2527/1992.701224x.

Armstrong DT. (1993). Recent advances in superovulation of cattle. Theriogenology 39:7-24. https://doi.org/10.1016/0093-691X(93)90021-V.

Blondin et al. (2002). Manipulation of follicular development to produce developmentally competent bovine oocytes. Biology of Reproduction 66:38-43. DOI: 10.1095/biolreprod66.1.38.

Bo, G.A. et al. (1994). Superovulatory response to a single subcutaneous injection of Folltropin-V in beef cattle. Theriogenology, Nov. 1, 1994, vol. 42, Issue 6, pp. 963-975. DOI: 10.1016/0093-691x(94)90119-4.

Callesen et al. (1986). Preovulatory endocrinology and oocyte maturation in superovulated cattle. Theriogenology 25:71-86. https://doi.org/10.1016/0093-691X(86)90184-6.

Cooke et al. (1997). Circulating FSH isoform patterns during recurrent increases in FSH throughout the oestrous cycle of heifers. J. of Reproduction and Fertility 110: 339-345. DOI: 10.1530/jrf.0.1100339.

Driancourt, MA. et al. (1992). Effect of superovulation with pFSH or PMSG on growth and maturation of the ovulatory follicles in sheep. Anim Reprod Sci; 27:279-292. https://doi.org/10.1016/0378-4320(92)90143-2.

Goff AK, Greve T, Bousquet D, King WA (1986). Progesterone and luteinizing hormone profiles in heifers used as oocyte donors. Theriogenology; 26:577-586. doi: 10.1016/0093-691x(86)90164-0. PMID: 16726223.

Hyttel et al. (1988). Ultrastructure of in-vivo fertilization in superovulated cattle. J. Reproduction and Fertility. 82:1-13. DOI: 10.1530/jrf.0.0820001.

Kimura, K. (2016). Superovulation with a single administration of FSH in aluminum hydroxide gel: a novel superovulation method for cattle. The Journal of Reproduction and Development, 62(5), 423-429. doi: 10.1262/jrd.2016-066.

Landry et al. (2016). Effect of cow age on the in vitro developmental competence of oocytes obtained after FSH stimulation and coasting treatments. Theriogenology 86: 1240-1246. DOI: 10.1016/j.theriogenology.2016.04.064.

Laster, DB. (1972). Disappearance of and uptake of 125I FSH in the rat, rabbit, ewe and cow. J. Reproduction and Fertility, 30:407-415. DOI: 10.1530/jrf.0.0300407.

Martins, CM, et al. (2012). The effect of timing of the induction of ovulation on embryo production in superstimulated lactating Holstein cows undergoing fixed-time artificial insemination. Theriogenology 78 (5) :974-980. DOI: 10.1016/j.theriogenology.2012.05.007.

Nivet et al. (2012). FSH withdrawal improves developmental competence of oocytes in the bovine model. Reproduction. Feb. 2012; 143(2):165-71. doi: 10.1530/REP-11-0391. Epub Nov. 11, 2011. PMID: 22080141.

Nivet et al. (2017). Influence of luteinizing hormone support on granulosa cells transcriptome in cattle. Anim Sci J. Jan. 2018;89(1):21-30. doi: 10.1111/asj.12856. Epub Aug. 25, 2017. PMID: 28840634.

Price, C.A et al. (1999). Effects of superovulation on endogenous LH secretion in cattle, and consequences for embryo production. Theriogenology, vol. 51, Issue 1, pp. 37-46, DOI: 10.1016/s0093-691x(98)00229-5.

Schams et al. (1977). Some studies of the pregnant mare serum gonadotrophin (PMSG) and on endocrine responses after application for superovulation in cattle. Control of Reproduction in the Cow. J. M. Sreenan (Ed.) (Martinus Nijhoff Publishers: The Hague), pp. 122-142.

Soumano K, Price CA. (1997). Ovarian follicular steroidogenic acute regulatory protein, low-density lipoprotein receptor, and cytochrome P450 side-chain cleavage messenger ribonucleic acids in cattle undergoing superovulation. Biol Reprod; 56:516-522. DOI: 10.1095/biolreprod56.2.516.

Takedomi, T. et al. (1995). Superovulation of holstein heifers by a single subcutaneous injection of FSH dissolved in polyvinylpyrrolidone . . . Theriogenology. May 1995;43(7):1259-68. doi: 10.1016/0093-691x(95)00097-r. PMID: 16727711.

Tríbulo, Andrés et al. Superstimulation of ovarian follicular development in beef cattle with a single intramuscular injection of Folltropin-V. Animal Reproduction Science, Nov. 2011;129(1-2):7-13. doi: 10.1016/j.anireprosci.2011.10.013. Epub Nov. 6, 2011. PMID: 22115521.

Yadav, M.C. et al. (1986). Plasma concentrations of luteinizing hormone and progesterone during superovulation of dairy cows using follicle stimulating hormone or pregnant mare serum gonadotrophin. Theriogenology, vol. 26, Issue 4, 523-540. https://doi.org/10.1016/0093-691X(86)90043-9.

Yamamoto, M. et al. (1994). Superovulation in the cow with a single intramuscular injection of FSH dissolved in polyvinylpyrrolidone. Theriogenology. Feb. 2, 1994;41(3):747-55. doi: 10.1016/0093-691x(94)90184-k. PMID: 16727429.

* cited by examiner

1

SINGLE-INJECTION METHODS AND FORMULATIONS TO INDUCE AND CONTROL MULTIPLE OVARIAN FOLLICLES IN BOVINE, CAPRINE, OVINE, CAMELID AND OTHER FEMALE ANIMALS

CROSS-REFERENCE TO RELATED APPLICATIONS

This application is a continuation-in-part (CIP) of U.S. Ser. No. 17/828,412 filed May 31, 2022, which is a divisional of U.S. patent application Ser. No. 15/912,101, filed Mar. 5, 2018, now U.S. Pat. No. 11,376,220, which claims the benefit of priority date of U.S. Provisional Patent Application Ser. No. 62/527,084, filed Jun. 30, 2017, entitled SIMPLIFIED, SINGLE-INJECTION METHOD TO INDUCE AND CONTROL THE SYNCHRONOUS GROWTH AND OVULATION OF MULTIPLE OVARIAN FOLLICLES (SUPEROVULATION) IN BOVINE, OVINE, CAMELID AND OTHER FEMALE ANIMALS. The contents of these applications are herein incorporated by reference in their entirety.

FIELD OF THE INVENTION

The present invention relates to animal husbandry and the reproductive management process commonly referred to as embryo transfer (ET) technology. More specifically, the present invention is directed to simplified, single-injection methods and formulations to induce and control the synchronous growth (superstimulation), and ovulation (superovulation) of multiple ovarian follicles in bovine, caprine, ovine, camelid and other female animals enabling the subsequent collection of (a) multiple oocytes when conducting steps in the process generally referred to as in-vitro fertilization, or (b) multiple embryos when conducting steps in the process generally referred to as multiple ovulation embryo transfer.

BACKGROUND OF THE INVENTION

One of the reproductive management processes within animal husbandry is commonly referred to as embryo transfer (ET) technology which is comprised of the two sub-disciplines of in-vitro fertilization (IVF), and multiple ovulation embryo transfer (MOET). Both sub-disciplines deliver the same outcome of multiple embryos which are then transferred immediately into uteri of surrogate hosts, or frozen for transfer later.

IVF uses exogenous follicle stimulating hormone (FSH) for ovarian superstimulation causing multiple follicles to synchronously grow and mature. Prior to natural ovulation, the oocytes are harvested manually via ultrasound-guided oocyte pick-up (OPU), then, in the lab, oocytes are allowed to undergo in vitro maturation (IVM), are fertilized in a petri dish (IVF) to create embryos, which are cultured (IVC) for 7-8 days prior to transfer or freezing.

MOET uses exogenous FSH for ovarian superovulation causing multiple follicles to synchronously grow, mature and ovulate. The ovulated oocytes are fertilized in-vivo and then recovered from the uterus as embryos 7 days later for transfer or freezing. Both IVF and MOET feature the physiology of, and requirement for exogenous FSH as the crucial, must-have hormone component of embryo transfer technology. IVF and MOET are typically used on high-genetic-value females in a species which normally ovulate only one oocyte per estrous cycle (monovulatory) resulting in one offspring born per gestation cycle. When that same female is placed into a MOET program she is referred to as an embryo donor and has the potential (bovine, for example) to produce 50-100 viable embryos annually resulting in 35-70 offspring born via surrogate embryo recipients per 12 months.

While MOET has been practiced commercially for the past 40 years, commercial acceptance of IVF produced embryos began approximately 10 years ago.

Existing methods and systems for IVF and MOET include: EP0021234B1, EP0298990B1, U.S. Pat. Nos. 3,499,445, 3,835,108, 3,860,701, 4,005,063, 4,008,209, 4,159,980, 4,670,419, 4,762,717, 4,780,451, 4,975,280, 5,162,306, 5,512,303, 5,589,457, 5,633,014, 5,650,173, 5,747,058, 5,941,844, 6,028,057, 6,573,254, 7,151,083, 7,205,281, 7,446,090, 7,740,884, 7,741,268, 8,530,419, 8,905,913, 8,927,496, 8,937,044, 9,018,165, 9,351,818, 9,352,011, US20050130894, US20060264372, US20070173450, US20070197435, US20090036384, US20120046519, US20130041210, US20130085321, CN101129333A, CN104800834A, U.S. Pat. Nos. 4,599, 227, 7,563,763, 7,629,113, 8,518,881, US20080312151, US20140335193, US20150335713, US20160250333, WO199516459A1.

IVF oocyte donors typically require four to six injections of FSH over two-three days while MOET donors require eight FSH injections administered over four days.

To satisfy the genetic and financial objectives of the donor's owner, the impetus for incorporating multiple ovulation and embryo transfer (MOET) and/or trans-vaginal ovum pick-up (OPU) coupled with IVF into a reproductive management program for bovine livestock and other animals has been to increase the reproductive rates of females which have demonstrated desirable reproduction, mothering and/or production traits, or due to genomic testing are likely to possess and express desirable reproduction, mothering and/or production traits in their offspring. MOET is not possible in the absence of superovulation and approximately half of the animals worldwide subjected to OPU, notably *Bos taurus* donors incorporate a superstimulation protocol to yield follicles which contain healthy, mature oocytes appropriate for OPU, IVF and culture.

Known superovulation protocols for MOET can be repeated every five to seven weeks and on average produce a sevenfold viable (transferrable) embryo increase per occasion, and an eleven-fold or more per lifetime increase in recoverable, viable embryos when compared to using no assisted reproductive technologies in a species. In the absence of superovulation protocols, a single viable embryo can be recovered approximately sixty percent of the time from a non-stimulated donor, and that requires the collection being performed by experienced technicians. Under similar conditions, known superovulation methods yield an average of seven transferrable or freezable embryos per superovulation although the variation is wide in number. Due to an assortment of reasons, no viable embryos are recovered from 15% of superovulation attempts. A small percentage of superovulated donors yield more than twenty transferrable/freezable embryos per superovulation; and very rarely, more than fifty. Known superstimulation protocols for IVF donors on average produce a threefold viable (transferrable) embryo increase per oocyte pickup session, which can be repeated every two to three weeks.

Two known methods for superovulating bovine animals have been based on using one of two different gonadotropins, specifically FSH or PMSG. Gonadotropins are glycoprotein polypeptide hormones secreted in most vertebrates and include the mammalian hormones follicle-stimulating hormone (FSH), luteinizing hormone (LH), placental/chorionic gonadotropins human chorionic gonadotropin (hCG) and equine chorionic gonadotropin (eCG) which is also referred to as pregnant mare serum gonadotropin (PMSG). These hormones are central to complex endocrine system regulation, normal growth, sexual development, and reproductive function. The hormones LH and FSH are secreted by the anterior pituitary gland, while hCG and eCG (PMSG) are secreted by the placenta in pregnant humans and mares, respectively. Veterinary-use PMSG (which is not US FDA approved) is indicated for estrus synchronization in sows and laboratory animals. Veterinary-use FSH is US FDA approved and is indicated for the induction of superstimulation and superovulation in beef and dairy heifers and cows.

A known first method of inducing superovulation was to administer off-label an intramuscular injection of 1800-3000 IU of pregnant mare serum gonadotropin (PMSG), followed by LH or GnRH and prostaglandin F2 alpha. A second prostaglandin injection was often given twelve-to-twenty hours after the first, which typically improved embryo production. Unfortunately, PMSG never became the popular "gold standard" superovulatory agent due to its unpredictability to generate a superovulatory response, and due to the extreme range of viable embryo yield when the hormone did stimulate. These problems with PMSG are thought to be associated with a reduced ability to deliver an LH surge, and to PMSG's very long half-life (>40 hours) which results in the undesired continued recruitment of follicles after ovulation. The systemic physiological half-life of FSH is 5 hours in the cow.

A second known method of superovulation which has been the gold standard protocol the past 40 years due to its predictable embryo yield is to administer eight injections of follicle stimulating hormone (FSH) at half-day intervals. Prior to and throughout FSH treatment, a progesterone (P4) impregnated device is placed vaginally which maintains high, sustained systemic P4. Lutalyse (dinoprost) or Estrumate (D-cloprostenol) is injected 72 to 96 hours after initiation of treatment along with the sixth, seventh or eighth FSH injection. A common decreasing dose, two injections per day FSH regimen is 15 iu 2×, 11 iu 2×, 7 iu 2×, and 4 iu 2×, administered at 12-hour intervals over four days with Estrumate or Lutalyse injected with the sixth, seventh or eighth FSH injection. In addition to the eight FSH injections, an injection of GnRH (gonadotropin releasing hormone) is normally administered two days before the start of FSH which serves to stimulate the release of endogenous LH, which causes rupture (removal) of the dominant ovarian follicle thereby prompting a new wave of follicular growth to begin. A second GnRH injection is routinely administered in MOET programs two days after the final FSH injection to stimulate the release of endogenous LH to control and predict the donor's ovulation period. This second GnRH injection is administered with the hope and desire that it will manipulate, stimulate and control the onset of the donor's LH surge culminating in synchronous ovulation over a desired period of time resulting in a high fertilization rate. Endogenous GnRH originates in the hypothalamus and travels systemically to the pituitary gland with the expectation that as a releasing hormone, it will travel systemically to the pituitary and stimulate the critical pulsatile releases of LH (the LH surge) from the pituitary which then travels systemically to the ovaries to induce synchronous and complete ovulation over a time period. Unfortunately, the addition of exogenous GnRH during a MOET procedure does not always result in synchronous nor complete ovulation of all matured follicles, both of which are required to achieve a high fertilization rate and high embryo yield. Physiologically LH is the hormone directly responsible for the induction of synchronous and complete ovulation, not GnRH. Historically as well as currently, the popular GnRH-FSH-GnRH MOET protocol requires injecting the animal at minimum 10 different times over eight-nine days.

There is no FDA approved veterinary-use LH in the US. For that reason, current, popular superovulation protocols in the US inject GnRH prior to the start of FSH injections to stimulate the endogenous release of LH to cause removal of the dominant follicle. GnRH is injected once again 8-9 days later (after FSH has stimulated growth and maturity of follicles) to initiate the chain of events previously described in paragraph 12 leading to ovulation. Administering exogenous GnRH does not explicitly achieve the end-goal of ovulation, and physiologically GnRH is not directly responsible for causing ovulation, versus administering LH which is the hormone directly responsible for ovulation.

Disadvantageously however, today's gold-standard superovulation protocol is rather inefficient overall due to all known inducing agents having a very short biological half-life of 0.3-5.0 hours which mandates repeated dosing at specific timed intervals throughout a donor's superovulation or superstimulation period. The protocol is inefficient due to repeated dosing requirements (10 injections for MOET, 4-6 for OPU) of donor animals with stimulating and/or releasing/inducing agents on prescribed days at 12-hour intervals over 8-9 days. The protocol can be challenging for the veterinarian or cattle/animal owner to comply with. The current protocol is (a) difficult to achieve 100% compliance because it requires strict attention to multiple details and personnel over 8-9 days at locations normally distant from the MOET or OPU technician; (b) it is time and labor intensive (therefore costly) requiring dedicated on-farm or in-clinic personnel on at least ten occasions at defined times and days to identify, gather, confine, physically restrict and lastly inject the MOET or IVF donor(s); (c) the current protocol subjects donors and personnel to stress and potential physical injury; and (d) the increased donor stress associated with the gathering/handling and injection sequence has been shown to negatively affect the donor's superovulatory response, fertilization rate and milk production. The entire mandated sequence (initial GnRH injection followed by twice daily FSH injections, concluding with a final GnRH injection) is stressful to the donor animals, and subjects personnel and donors to the increasing exposure for physical injury with each sequential requirement to gather, confine, restrain and inject animals often weighing 1500 pounds or more.

Thus, it is desired to provide method and formulations that solve the disadvantages in the prior art for superstimulation and superovulation protocols.

SUMMARY OF THE INVENTION

It is an object of the present invention to provide a method and system that solves the disadvantages in the prior art superovulation and superstimulation protocol for bovine animals. In addition, it is an object of the present invention to provide a method and system that solves the disadvantages in the prior art superovulation and superstimulation protocol for caprine, ovine, camelid and other female animals.

It is an object of the present invention to provide a method and formulation for a simplified, single-injection method to induce and control the synchronous growth (superstimulation), and ovulation (superovulation) of multiple ovarian follicles in bovine, caprine, ovine, camelid and other female animals enabling the subsequent collection of (a) multiple oocytes if conducting via in-vitro fertilization, or (b) multiple embryos if conducting via multiple ovulation embryo transfer.

It is an object of the present invention to provide a sustained, controlled release method and formulation that involves administering a drug formulation in a single administration for inducing and controlling the synchronous growth (superstimulation) and ovulation (superovulation) of multiple ovarian follicles in bovine, ovine, caprine, camelid and other female animals.

It is an object of the present invention to provide a drug formulation comprising a dual-hormone protein microsphere matrix of animal origin encapsulated by an engineered controlled release agent.

It is an object of the present invention to provide a drug formulation that induces dominant follicle removal via LH and induces synchronous stimulation and growth of multiple ovarian follicles via FSH. It is an object of the present invention to use recombinant FSH and to use recombinant FSH within the formulations and methods described herein.

It is an object of the present invention to provide a drug formulation that controls the magnitude and duration of FSH stimulation via engineered controlled release technology agents.

It is an object of the present invention to provide a drug formulation that controls the timing of and induces the synchronous ovulation of the now-mature follicles via an engineered controlled release technology LH surge.

It is an object of the present invention to provide systems and methods for administering a protein microsphere matrix to an animal, the protein microsphere matrix including a controlled release agent, wherein the step of administering the protein microsphere matrix to the bovine animal is performed via a single administration, and wherein the protein microsphere matrix induces superstimulation when used for IVF, or superstimulation with accompanying superovulation when used in the animal for MOET.

It is an object of the present invention to provide a formulation that accomplishes via 2 hormones, as a single injection, specifically: removal of the dominant follicle by LH, followed by superstimulation (or superovulation) by FSH, followed by an engineered LH surge resulting in ovulation per a defined time schedule. In certain objects of the invention recombinant FSH is used.

It is an object of the present invention for engineered controlled release LH in the formula to have two advantageous effects: (1) dominant follicle removal (DFR) immediately upon injection; and (2) 8-9 hours later, a second engineered dose of LH is released over several hours in increasing "bursts" culminating in and directly causing synchronous ovulation.

It is an object of the present invention to provide methods and systems that include all of the above advantages and combinations of all the above objects and advantages.

These and other objects of the invention are achieved by providing a method of inducing superovulation in bovine animals comprising the steps of administering a protein microsphere matrix having a diameter ranging from 50-70 microns to an animal, the protein microsphere matrix including a controlled release agent, wherein the step of administering the protein microsphere matrix to the animal is performed via a single administration, and wherein the protein microsphere matrix induces superovulation in the animal.

In certain embodiments, the protein microsphere matrix includes an active pharmaceutical ingredient (API).

In certain embodiments, the API is FSH and/or LH.

In certain embodiments, the FSH is non-recombinant FSH. In certain embodiments, recombinant FSH is used.

In certain embodiments, the protein microsphere matrix comprises at least one polymer.

In certain embodiments, the protein microsphere matrix comprises polylactide (PLA) or polylatic co-glycolic acid (PGLA).

In certain embodiments, the protein microsphere matrix comprises an organic polymer.

In certain embodiments, at least one polymer includes poly (dl-lactide), lactide/glycolide copolymers, sucrose acetate isobutyrate (SAIB, i.e. SABER platform), and lactide/caprolactone copolymers.

In certain embodiments, the matrix includes an emulsifier. In certain embodiments, the emulsifier is sucrose acetate isobutyrate (SAIB).

In certain embodiments, the matrix includes a solvent that allows it to be administered through a small-gauge needle.

In certain embodiments, the matrix is administered via injection or via an in-situ gel upon intramuscular injection for controlled release of API.

In certain embodiments, superovulation in the bovine animal involves stimulating at least two primordial follicles in the bovine animal to mature simultaneously.

In certain embodiments, the controlled release agent includes a prescribed dose of follicle stimulating hormone (FSH) and/or luteinizing hormone (LH).

In certain embodiments, the API is a dual hormone treatment.

In certain embodiments, the controlled release LH agent causes immediate regression of the dominant follicle in the animal. It is an object of the present invention where the regression of the dominant follicle begins immediately post administration of the controlled release agent.

In certain embodiments, FSH is provided at a measured, controlled rate during hours 48-144 post administration.

In certain embodiments, FSH is provided at a measured, controlled rate during hours 48-168 post administration.

In certain embodiments, FSH is provided at a measured, controlled rate during hours 40-168 post administration.

In certain embodiments, the controlled release agent includes a calculated, pulsatile release of LH between hours 145-182 post administration.

In certain embodiments, the controlled release agent includes a calculated, pulsatile release of LH between hours 168-182 post administration.

In certain embodiments, the LH surge causes follicles in the bovine animal to ovulate.

In certain embodiments, the controlled release agent includes only a single dose of follicle stimulating hormone (FSH). In certain embodiments, the controlled release agent includes only a single dose of recombinant follicle stimulating hormone (FSH)

In certain embodiments, the controlled release agent includes two controlled release doses of LH with each LH dose releasing into the bloodstream days apart.

In certain embodiments, the controlled release agent includes only a single dose of gonadotropin releasing hormone (GnRH).

In certain embodiments, the GnRH will indirectly stimulate an endogenous LH surge to culminate in synchronous ovulation.

In certain embodiments, GnRH will indirectly eventually cause DFR.

In certain embodiments, GnRH is encapsulated and included with FSH. In certain embodiments, GnRH is encapsulated and included with recombinant FSH.

Other objects of the invention are achieved by providing a drug formulation for inducing superovulation in bovine animals, the formulation comprising a protein microsphere matrix having a diameter ranging from 50-70 microns to an animal; a controlled release agent, wherein the drug formulation induces superovulation of a bovine animal when administered to the animal.

In certain embodiments, the method induces superovulation in female cattle, sheep, goats, camels and other traditionally mono-ovular species of animals other than humans.

In certain embodiments, the formulation is a suspension or is an extended release powder for suspension.

In certain embodiments, the engineered protein microsphere matrix comprises at least one polymer.

In certain embodiments, the protein microsphere matrix comprises poly lactic acid (PLA) or poly lactide-co-gly-colide (PLGA).

In certain embodiments, the protein microsphere matrix is suspended in a buffer.

In certain embodiments, the controlled release agent includes a prescribed dose of follicle stimulating hormone (FSH) and/or luteinizing hormone (LH). In certain embodiments, the controlled release agent includes a prescribed dose of recombinant follicle stimulating hormone (FSH) and/or luteinizing hormone (LH).

In certain embodiments, the controlled release agent includes only a single dose of follicle stimulating hormone (FSH) or recombinant follicle stimulating hormone.

In certain embodiments, the controlled release agent includes two controlled release doses of LH with each LH dose releasing into the bloodstream days apart.

In certain embodiments, the controlled release agent includes) only a single dose of gonadotropin releasing hormone (GnRH).

In certain embodiments, the GnRH will indirectly stimulate an endogenous LH surge to culminate in synchronous ovulation.

In certain embodiments, GnRH will indirectly eventually cause DFR.

In certain embodiments, GnRH is encapsulated and included with FSH or recombinant follicle stimulating hormone.

Other objects of the invention are achieved by providing a single controlled released dose of LH hormone that is comprised of multiple controlled LH surges. In certain embodiments, the controlled release dose of LH hormone will lyse the dominant follicle on the front end of the process between hours 0-18 (hour 0 is when the drug is injected), and 6 days later the second controlled release LH-surge will induce/direct ovulation per a desired time schedule. This second controlled release "LH-surge" is characterized by 3-8 increasingly potent LH releases between hours 144-180.

In certain embodiments, the formulation yields FSH, and the FSH extraction process also yields the "by-product" of LH.

In certain embodiments, a single-injection FSH formulation includes controlled release GnRH instead of LH as a component of the single-injection FSH product.

In certain embodiments, the formulation replaces the 2 GnRH injections with a single LH injection.

Other objects of the invention are achieved by providing a method for multiple ovulation embryo transfer (MOET) comprising administering a dual hormone formula comprising a prescribed volume of LH and FSH to a bovine animal, wherein the LH in the dual hormone formula is available immediately to the bloodstream of the bovine animal, while the FSH is available to the bloodstream of the bovine animal via an engineered controlled release.

In certain embodiments, the formula is administered by an injection.

In certain embodiments, the dual hormone formula is for dominant follicle removal.

In certain embodiments, the FSH is released over 4 days after the administration of the dual hormone formula.

In certain embodiments, the controlled release of FSH causes follicles to grow and mature.

In certain embodiments, the controlled release of FSH is followed by a controlled release LH surge resulting in ovulation.

Other objects of the invention are achieved by providing a method for IVF comprising administering a dual hormone formula comprising a prescribed volume of LH and FSH to a bovine animal, wherein the LH is available immediately to the bloodstream of the bovine animal, while the FSH is available to the bloodstream of the bovine animal via an engineered controlled release formulation.

In certain embodiments, the formula is administered by an injection.

In certain embodiments, the dual hormone formula is for dominant follicle removal.

In certain embodiments, the FSH is released over 4 days after the administration of the dual hormone formula.

In certain embodiments, the controlled release of FSH causes follicles to grow and mature.

In certain embodiments, the controlled release of FSH causes superstimulation, but does not result in an LH surge in the bovine animal.

Other objects of the invention are achieved by providing a biodegradable controlled release (CR) polymer system to a bovine animal.

In certain embodiments, the system includes an intramuscular (IM) injection of controlled release (CR) microparticles.

In certain embodiments, the CR microparticles are molecules of API (FSH/LH) encapsulated in engineered thicknesses of poly lactide-co-glycolide (PLGA).

In certain embodiments, as the PGLA layer biodegrades at various engineered times, the API (FSH, or FSH/LH, or FSH/GnRH) is released into the bloodstream.

In certain embodiments, the CR microparticles are then placed into a "liquid polymer matrix solution."

In certain embodiments, when the encapsulated CR microparticle solution is injected and contacts aqueous body fluids, it forms a solid (an in-situ gel, a "depot").

In certain embodiments, the release of the individual API encapsulated particles into the bloodstream occurs over time as the polymer in-situ gel matrix depot biodegrades and the API is released from the depot.

In certain embodiments, non-encapsulated API molecules can be "dissolved" into the liquid polymer matrix and enter circulation over time as the polymer in-situ gel degrades.

In certain embodiments, the engineered microparticles allow the API to be released at desired times.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

In the following description, numerous details are set forth for the purpose of explanation. However, one of ordinary skill in the art will realize that the invention may be practiced without the use of these specific details.

The application incorporates by reference the contents of U.S. Pat. No. 5,679,377 entitled "Protein Microspheres and Methods of Using Them."

In certain embodiments it is contemplated, a method of inducing superovulation in bovine animals comprises the steps of administering a protein microsphere matrix having a diameter ranging from 50-70 microns to a bovine animal, the protein microsphere matrix including a controlled release agent, wherein the step of administering the protein microsphere matrix to the bovine animal is performed via a single administration, and wherein the protein microsphere matrix induces over the course of 182 hours more/less the sequential outcomes of dominant follicle removal (DFR) via LH, superovulation via FSH, and onset of synchronous ovulation beginning at a prescribed time via LH surge in the bovine animal. In certain embodiments of the invention, recombinant follicle stimulating hormone is used for the formulations and methods described herein.

In certain embodiments, it is contemplated that the protein microsphere matrix comprises at least one polymer.

In certain embodiments, it is contemplated that the protein microsphere matrix comprises poly (lactide-co-glycolide) (PLGA) or poly (lactic acid) (PLA).

In certain embodiments, it is contemplated that the protein microsphere matrix comprises an organic polymer.

In certain embodiments, it is contemplated that superovulation in the bovine animal involves stimulating at least two primordial follicles in the bovine animal to mature simultaneously.

In certain embodiments, it is contemplated that the controlled release agent includes a single dose of follicle stimulating hormone (FSH) and zero to two doses of luteinizing hormone (LH).

In certain embodiments, it is contemplated that the controlled release agent includes a single dose of follicle stimulating hormone (FSH) and zero to two doses of gonadoptropin releasing hormone (GnRH).

In certain embodiments, it is contemplated that the controlled release agent causes immediate regression of the dominant follicle in the bovine animal via LH.

In certain embodiments, it is contemplated that the regression of the dominant follicle begins immediately post administration of the controlled release agent.

In certain embodiments, it is contemplated that FSH is provided at a constant, prescribed concentration for hours 48-144 more/less post administration.

In certain embodiments, it is contemplated that the controlled release agent includes a calculated surge (burst) of LH between hours 0-12, and again between hours 145-182 post administration.

In certain embodiments, it is contemplated that the LH surge causes follicles in the bovine animal to ovulate.

In certain embodiments, it is contemplated that the protein microsphere matrix is administered via a preferred intramuscular (IM) injection.

In certain embodiments, it is contemplated that the protein microsphere matrix is administered via a subcutaneous (SQ) method.

In certain embodiments, it is contemplated that the drug formulation for inducing superovulation in bovine animals comprise a protein microsphere matrix having a diameter ranging from 50-70 microns to a bovine animal; a controlled release agent, wherein the drug formulation induces superovulation of a bovine animal when administered to the bovine animal.

In certain embodiments, it is contemplated that the formulation is a suspension or is an extended release powder for suspension.

In certain embodiments, it is contemplated that the formulation is an in-situ gel.

In certain embodiments, it is contemplated that the protein microsphere matrix comprises at least one polymer.

In certain embodiments, it is contemplated that the protein microsphere matrix comprises poly(lactic acid) (PLA) or poly (lactide-co-glycolide) (PGLA).

In certain embodiments, it is contemplated that the protein microsphere matrix is suspended in a buffer.

In certain embodiments, it is contemplated that the controlled release agent includes a single dose of follicle stimulating hormone (FSH) and zero to two doses of luteinizing hormone (LH).

In certain embodiments, the agent is an engineered, sustained release complex.

In certain embodiments, the agent is an extended release powder for suspension, administered as a 10-15 ml IM single injection via 18 ga×1" or 1.5" needle.

In certain embodiments, the PLA or PGLA is the release rate controlling polymer.

In certain embodiments, the formulation is a single injection drug for veterinary use using two different hormones in a single dose to achieve desired, different FSH and LH release profiles.

In certain embodiments, the controlled release method would (a) cause immediate regression of the dominant follicle via LH dose, (b) beginning at 48 hours post injection, provide delivery of FSH to the target organs between hours 48-144, (c) followed by a calculated surge (burst) of LH between hours 145-182 post injection.

In certain embodiments, the formulation causes dominant follicle removal (DFR) allowing for a new wave of follicles to emerge. In certain embodiments, the superovulation causes the new wave of primordial follicles to mature simultaneously. In certain embodiments, the desired LH surge causes follicles to ovulate at a determined/desired time and over a desired short interval.

In certain embodiments, the formulation is biodegradable.

In certain embodiments, the formulation includes encapsulated microparticles or microspheres, or in-situ gel.

In certain embodiments, the biodegradable polymer provides for the parenteral delivery of a defined concentration and volume of FSH/LH throughout a specified time period.

In certain embodiments, the formulation is an Intramuscular (IM) or subcutaneous (SQ) injection of controlled-release (CR) microparticles. This option contains prescribed quantities of FSH & LH, encapsulated within a polymer having various thicknesses and/or dissolution rates, thereby allowing prescribed amounts of active pharmaceutical ingredients (API) to become released into the bloodstream at pre-determined, designed times.

In certain embodiments, the formulation is an IM injection resulting in an in-situ gel (i.e. a depot) which features biodegradable polymer CR precipitation technology. Biodegradable injectable in situ gel forming drug delivery consists of biodegradable polymers dissolved in a biocompatible carrier. When the liquid polymer system is aspirated from its vial and injected in the body using standard needles and syringes, it solidifies upon contact with aqueous body fluids to form a solid implant.

In certain embodiments, the formulation accomplishes via 2 hormones, as a single injection, specifically: removal of the dominant follicle by LH, followed by superstimulation (or superovulation) by FSH, followed by the engineered LH surge resulting in ovulation per a defined time schedule.

In certain embodiments, the formulation accomplishes via 2 hormones, as a single injection, specifically: removal of the dominant follicle indirectly by controlled release GnRH, followed by superstimulation (or superovulation) by FSH, followed by controlled release GnRH if for superovulation, which indirectly results in ovulation per a defined time schedule.

In certain embodiments, the API (i.e. the FSH/LH drug formulation which has not been formulated into CR microparticles) is incorporated into the polymer solution, it becomes entrapped within the polymer matrix as it solidifies. Drug release occurs over time as the polymer biodegrades, resulting in release of the FSH/LH drug formulation into the bloodstream of a female animal.

Example 1—MOET Study Proposal

Hour 0=when the single-intramuscular (IM) injection of the controlled release (CR) hormone compound containing FSH+LH is administered, delivering a controlled release of the compound for 182 hours more/less.

| Species | Cattle |
|---|---|
| Route | Intramuscular Injection (IM) |
| Injection Volume | 10-15 ml |
| Needle size | 18 ga × 1.5" preferred |
| Total Dose | 75 IU FSH & 50 mg LH |
| Desired MOET plasma profile | Hours 0-2: LH#1 is immediately available in the blood stream as 25 mg more/less of active hormone, targeting and causing ovulation (removal) of the dominant follicle(s) present on one or both of the ovaries |
| | Hours 48-144: FSH (75 IU more/less) is control-released over 4 days (more/less) to induce synchronous development of multiple ovarian follicles. The release pattern can be decreasing, increasing or level-dose throughout the release period |
| | Hours 145-182: LH#2 is control-released and functions as an exogenous LH surge targeting and causing the cohort of pre-ovulatory follicles to ovulate simultaneously |

In the study proposal as described in example 1, multiple test formulations are prepared utilizing PLA or PLGA (or both) polymers. Analytical methods are implemented to characterize the proteins in the microsphere matrix. The formulations are placed on in vitro release and analyzed to verify release rate over a four-day period. An option to produce a second formulation for an LH release between hours 145-182 post injection is also presented.

In certain embodiments, both microsphere formulations may be combined into a single dose to achieve the different FSH and LH release profile.

The scope of the formulation development phase consists of a single round with 8 microsphere formulations of Poly Active polymer which will be varied in polymer composition and water-to-polymer ratio in accordance with the target product profile as described in Table 2. The formulation rounds are at the 50 to 100 scale.

The process is engineered to produce microspheres in the 50-70 micron diameter range. This size range is suitable for delivery through an 18 ga needle.

TABLE 2

| Target product profile | |
|---|---|
| Duration of release (requested profile) | 4 days (zero order, <20% burst) |
| API dose | 75 IU for 96 hours |
| Injection volume | 10-15 ml |
| Administration route | IM |
| Needle size | 18 gauge (max) |

After preparation of the microspheres, a grinding method is applied to instantaneously release some of the encapsulated API. In case the microsphere processing activity caused protein degradation, this will be assessed by I-PLC and SOS-PHAGE analysis of the released protein.

The microspheres will be further analyzed for morphology, particle size distribution, and API content.

An in vitro release study will be performed, considering the intended duration of release and the burst requirements with maximum 10 time points (for example 1h, 6 h, 12 h, 24 h, 36 h, 48 h, 96 h). The in vitro samples will be analyzed by HPLC and SOS-PHAGE for activity.

An injectability study will be performed on one of the select prototype formulations. Microspheres shall be resuspended in buffer and drawn through successively smaller needle gauges. This study shall establish the optimal balance between microsphere concentration, injection volume and needle gauge.

Having thus described several embodiments for practicing the inventive method, its advantages and objectives can be easily understood. Variations from the description above may and can be made by one skilled in the art without departing from the scope of the invention.

Accordingly, this invention is not to be limited by the embodiments as described, which are given by way of example only and not by way of limitation.

REFERENCES

Alcivar A A. et al. 1992. Endocrine changes in beef heifers superovulated with follicle stimulating hormone (FSH-P) or human menopausal gonadotropin. J Anim Sci; 70:224-231.

Armstrong D T. 1993. Recent advances in superovulation of cattle. Theriogenology 39:7-24.

Blondin et al. 2002. Manipulation of follicular development to produce developmentally competent bovine oocytes. Biology of Reproduction 66:38-43

Bo, G. A. et al. 1994. Superovulatory response to a single subcutaneous injection of Follitropin-V in beef cattle. Theriogenology, Nov. 1, 1994, Vol. 42, Issue 6. Pages 963-975

Callesen et al, 1986. Preovulatory endocrinology and oocyte maturation in superovulated cattle. Theriogelology 25:71-86.

Cooke et alt 1997. Circulating FSH isoform patterns during recurrent increases in FSH throughout the oestrous cycle of heifers. J. of Reproduction and Fertility 110: 339-345.

Driancourt M A. et al. 1992. Effect of superovulation with pFSH or PMSG on growth and maturation of the ovulatory follicles in sheep. Anim Reprod Sci; 27:279-292.

Goff A K, Greve T, Bousquet D, King W A. 1986. Progesterone and luteinizing hormone profiles in heifers used as oocyte donors. Theriogenology; 26:577-586.

Hyttel et al, 1988. Ultrastructure of in-vivo fertilization in superovulated cattle. J. Reproduction and Fertility, 82:1-13.

KIMURA, K. Superovulation with a single administration of FSH in aluminum hydroxide gel: a novel superovulation method for cattle. The Journal of Reproduction and Development, 62(5), 423-429 (2016).

Landry et al. 2016, Effect of cow age on the in vitro developmental competence of oocytes obtained after FSH stimulation and coasting treatments. Theriogenology 86: 1240-1246.

Laster, D B, 1972. Disappearance of and uptake of 1251 FSH in the rat, rabbit, ewe and cow, J. Reproduction and Fertility, 30:407-415.

Martins, C M, et at. 2012, The effect of timing of the induction of ovulation on embryo production in superstimulated lactating Holstein cows undergoing fixed-time artificial insemination. Theriogenology 78 (5):974-980.

Nivet et al, 2012. FSH withdrawal improves developmental competence of oocytes in the bovine model. Reproduction (Cambridge, England). 143, 165-71. 10.1530/REP-11-0391.

Nivet et al. 2017. Influence of luteinizing hormone support on granulosa cells transcriptome in cattle. Anim Sci J. doi:10.1111/asj.12856

Price, C. A et al, 1999. Effects of superovulation on endogenous LH secretion in cattle, and consequences for embryo production, Theriogenology, Volume 51, Issue 1, 37-46, Schams et al. 1977. Some studies of the pregnant mare serum gonadotrophin (PMS G) and on endocrine responses after application for superovulation in cattle. Control of Reproduction in the Cow. Martinus Nijhoff, The Hague, pp 122-142, Soumano K, Price C A. 1997. Ovarian follicular steroidogenic acute regulatory protein, low-density lipoprotein receptor, and cytochrome P450 side-chain cleavage messenger ribonucleic acids in cattle undergoing superovulation. Biol Reprod; 56:516-522.

Takedomi, T. et al. Superovulation of holstein heifers by a single subcutaneous injection of FSH dissolved in polyvinylpyrrolidon. Theriogenology, Volume 43, Issue 7, Pages 1259-1268

Tribulo, Andrés et al. Superstimulation of ovarian follicular development in beef cattle with a single intramuscular injection of Follitropin-V. Animal Reproduction Science, Volume 129, Issue 1, Pages 7-13.

Yadav, M. C. et al. 1986. Plasma concentrations of luteinizing hormone and progesterone during superovulation of dairy cows using follicle stimulating hormone or pregnant mare serum gonadotrophin. Theriogenology, Volume 26, Issue 4, 523-540.

Yamamoto, M. et al. Superovulation in the cow with a single intramuscular injection of FSH dissolved in polyvinylpyrrolidon Theriogenology, Volume 41, Issue 3, Pages 747-755.

The invention claimed is:

1. An injectable drug formulation for inducing ovarian follicular hyperstimulation and superovulation in bovine, caprine, ovine, camelid and other female animals, the formulation comprising:

an in-situ depot formulation comprising a protein microsphere matrix having a diameter ranging from 50-100 microns to a bovine animal, the protein microsphere matrix including controlled release agents, the controlled release agents including a single dose of recombinant follicle stimulating hormone (FSH) released over 96 hours beginning 48 hours after administration, and two doses of luteinizing hormone (LH), wherein the first dose of LH provides an immediate surge of LH and the second dose provides at least one calculated LH release (burst) after 144 hours from administration of the protein microsphere matrix, wherein the drug formulation is configured to be administered in a single administration of said protein microsphere matrix to a bovine animal, thereby inducing ovarian follicular hyperstimulation and superovulation of the bovine animal when administered to the bovine animal, wherein the protein microsphere matrix comprises at last one polymer, wherein the at least one polymer is selected from a group consisting of polyethylene glycol (PEG), poly(lactic acid) (PLA) or poly(lactide-co-glycolide) (PLGA).

2. The formulation of claim 1, wherein the formulation is a suspension or an extended release powder for suspension.

3. The formulation of claim 1, wherein the dose of recombinant FSH is 75 IU and the dose of LH is 50 mg.

4. The method of claim 1, wherein the first dose of LH provides a surge (burst) of LH between hours 0-12 from administration of the protein microsphere matrix.

5. The formulation of claim 1, wherein the second dose of LH provides two or more calculated LH releases.

6. The formulation of claim 1, wherein the second dose of LH provides 2-8 calculated LH releases between hours 145-182 from administration of the protein microsphere matrix.

7. The formulation of claim 1, wherein administration of the formulation to a bovine animal causes at least two primordial follicles in a bovine animal to mature simultaneously.

8. The formulation of claim 1, wherein recombinant FSH is provided at a prescribed rate for hours 48-144 post administration.

9. The formulation of claim 1, wherein the dose of recombinant FSH ranges from 35 to 75 IU.

* * * * *